United States Patent [19]

Godley

[11] Patent Number: 5,295,950
[45] Date of Patent: Mar. 22, 1994

[54] EAR PRESSURE DRESSING

[76] Inventor: Frederick A. Godley, 4 Rogers Ave., North Kingstown, R.I. 02852

[21] Appl. No.: 964,420

[22] Filed: Oct. 21, 1992

[51] Int. Cl.⁵ .................. A61F 13/00; A61F 15/00; A61F 13/12
[52] U.S. Cl. .................................. 602/53; 602/58; 602/74
[58] Field of Search .......................... 602/58, 74, 53

[56] References Cited

U.S. PATENT DOCUMENTS

| 3,520,306 | 7/1970 | Gardner et al. | 602/58 X |
| 3,529,597 | 9/1970 | Fuzak | 602/58 |
| 3,823,713 | 7/1974 | Shah | 602/74 |
| 4,534,342 | 8/1985 | Paxa | 602/74 |

Primary Examiner—Randall L. Green
Assistant Examiner—Elizabeth M. Burke
Attorney, Agent, or Firm—Salter, Michaelson & Benson

[57] ABSTRACT

A pressure dressing for use in the treatment of an auricular hematoma or other ear injury is formed from a thin strip of ductile metal having first and second spaced end portions which are joined by a central connector portion. A pair of foam sponge pads are adhesively affixed to an inner surface of the first and second end portions. In use, the connector portion is reversely bendable to position the pressure pads in closely spaced, substantially adjacent relation on opposing sides of the ear. The pads engage with opposing sides of the ear and exert pressure thereon so that blood does not reaccumulate in the injured area. The dressing may further include one or more tongue or arm portions which extend outwardly from the end portions and are bendable over and around the cartilaginous rim portions of the ear to maintain the dressing in position during periods of physical activity.

9 Claims, 2 Drawing Sheets

EAR PRESSURE DRESSING

BACKGROUND OF THE INVENTION

The instant invention relates to surgical pressure dressings and more particularly to a pressure dressing for use in the treatment of an auricular hematoma or other ear injury requiring pressure on the injured area.

An auricular hematoma is typically caused by a blunt trauma or shearing force to the external ear that disrupts the adherence of the perichondrium or skin of the ear to the underlying cartilage and the subsequent filling of the subperichondrial space with blood. Most auricular hematomas occur in the concavities on the anterior side of the ear because the anterior skin is closely fixed and firmly adherent to the underlying cartilage and therefore it will tend to shear off rather than slide over the cartilage. In contrast, the posterior skin of the ear is separated from the cartilage by muscle, fat and other tissue and is only loosely fixed to the cartilage. The posterior skin is therefore much more resistant to the shearing forces than the anterior skin.

Blunt trauma or shearing forces to the ear are typically inflicted during contact sports, such as wrestling and boxing. Because of the repeated trauma to the ear in these sports, auricular hematomas in wrestlers and boxers have traditionally been quite difficult to treat. In addition, many active athletes refuse to take the time off that is necessary for the hematoma to properly heal and for the skin to reattach to the cartilage. In the past it was common for wrestlers to line up after a match to have their ears "needled" to aspirate the accumulated blood. Many athletes refused the treatments because of excessive pain and as a result the untreated injuries usually resulted in a thickened deformity of the ear known as "cauliflower ear".

The standard approach in the treatment of an auricular hematoma is aspiration of the hematoma by a large bore needle, reapposition of the skin to the cartilage, prevention of hematoma reoccurrence, and the avoidance of infection. Most of the problems in the treatment of an auricular hematoma ar encountered with reapposition of the perichondrium to the underlying cartilage and the prevention of hematoma reoccurrence. Several surgical procedures have heretofore been known, but few have met with anything but limited success. One such procedure is to suture pressure dressings to the ear on opposing sides of the injured portion thereof. The pressure dressings are positioned on opposing sides of the ear and the sutures are passed through the cartilage to gently squeeze the skin and cartilage together between the dressings. This method often does not provide an evenly distributed pressure over the injured area and as a result, blood can reaccumualte under the skin to reform the hematoma. Reformation of the hematoma requires repeated aspiration of the accumualted blood which in turn increases the chance of infection. In addition, the procedure can sometimes be painful because several sutures are typically required to cover the entire area of the hematoma. Still further, the pressure dressing must be left in position for several weeks until the skin has reattached. For athletes who continue to participate in contact sports such as wrestling, these pressure dressings make the ear vulnerable to re-injury. The exposed dressing can easily be torn out during contact activity even if the ear is protected by head gear.

Another procedure which has had some success is to suture the detached skin and underlying cartilage together with absorbable mattress sutures. This procedure provides an evenly distributed pressure over the area of the injury and does not require the bulky pressure dressings of the previously described procedure, but it does have several disadvantages. The procedure requires several through and through sutures to completely cover the area of the hematoma and this can often be painful. The sutures can also irritate the ear tissue if they do not become absorbed quickly enough.

In addition to use in the treatment of auricular hematomas, pressure dressings are also used in many other treatments of the ear, such as the covering and compressing of an acute wound to the ear, the excision of a skin cancer, the placement of a skin graft, the repair of a torn earlobe, the treatment of a localized burn, or the excision of a keloid which can form on the earlobe or other portions of the ear after piercing thereof.

SUMMARY OF THE INVENTION

The instant invention provides a formable pressure dressing for use in the treatment of an auricular hematoma or other ear injury requiring pressure to prevent the reaccumulation of blood in the injured area.

Briefly, the instant invention comprises a thin strip of ductile metal having first and second spaced end portions which are joined by a central connector portion. A pair of foam sponge pads are affixed on the inner surfaces of the end portions. In use, the connector portion is reversely bent so that the sponge pads are positioned in closely spaced, substantially adjacent relation on opposing sides of the injured portion of the ear. The pads are further compressed together to engage with the ear on opposing sides thereof and exert pressure thereon to prevent blood from reaccumulating in that area. A first embodiment of the pressure dressing of the present invention is particularly useful in the treatment of an auricular hematoma. This embodiment includes spaced arm portions which extend outwardly from the end portions. When the dressing is located on the upper portion of the ear these arm portions are bent around the peripheral cartilaginous rim portions of the ear to maintain the dressing in position. A second embodiment of the ear pressure dressing of the present invention is useful for treating injuries to the earlobe. This embodiment includes a tongue portion which extends outwardly from the second end portion. When the dressing is located on the earlobe, the tongue portion is bent over and around a lower cartilaginous rim portion of the ear adjacent the earlobe. Neither of the ear pressure dressings require the use of sutures to maintain them in place and they are also easily removable for cleaning and examination of the ear during the treatment period. The dressings are comfortable to wear and are small enough so that they can be worn during physical activities, such as boxing and wrestling.

Accordingly, it is an object of the invention to provide a pressure dressing which does not require the use of surgical sutures.

It is another object to provide a pressure dressing which is formable to the particular shape or size of the patient's ear.

It is yet another object to provide a pressure dressing which is easily removable for periodic examination and cleaning of the ear, and then is easily replaceable for continued use.

It is still another object to provide a pressure dressing which is comfortable to wear, and which can be worn by wrestlers or boxers during practice or competition.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention.

DESCRIPTION OF THE PREFERRED EMBODIMENTS

Figure 1:
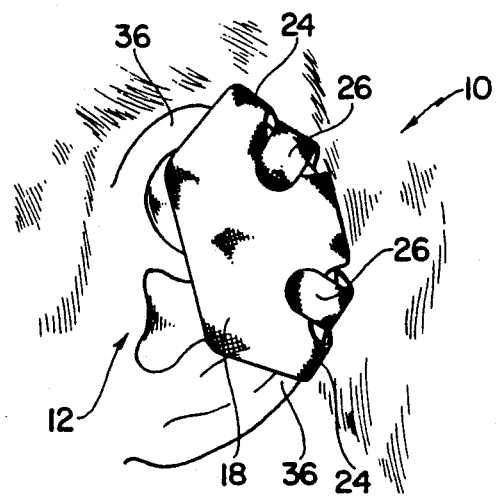
FIG. 1 is an elevational view of the ear pressure dressing of the instant invention mounted on an upper portion of an ear.
Figure 2:
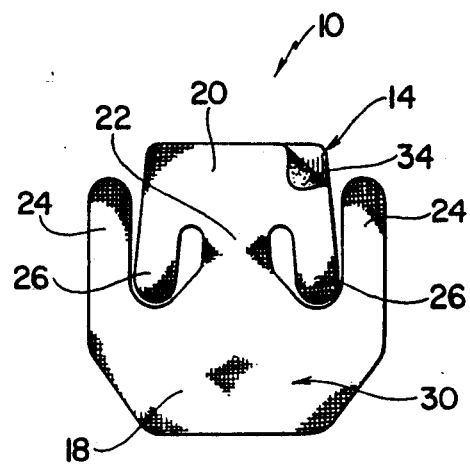
FIG. 2 is an elevational view of the outer surface of the unformed dressing.
Figure 3:
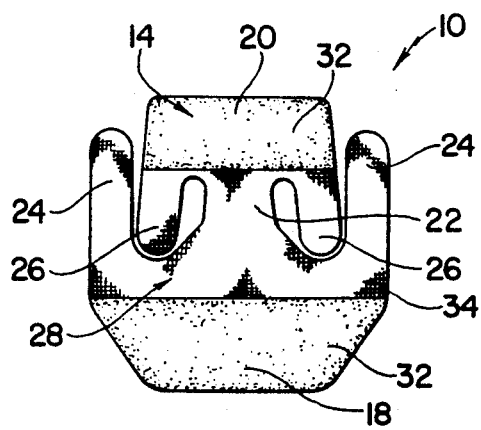
FIG. 3 is an elevational view of the inner surface of the unformed dressing.
Figure 4:
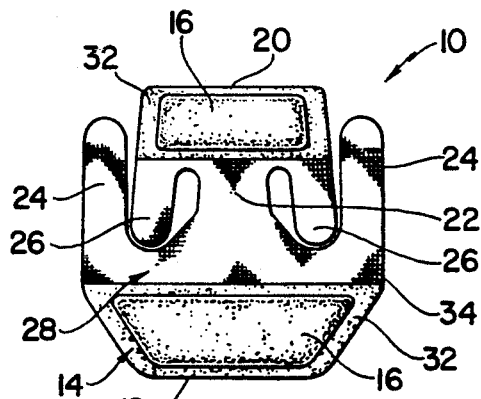
FIG. 4 is a view similar to FIG. 3 with the foam pads affixed to the end portions thereof.
Figure 5:
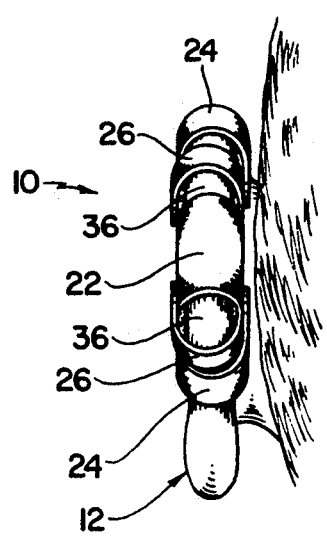
FIG. 5 is a rear view of the pressure dressing mounted on an upper portion of the ear.
Figure 6:
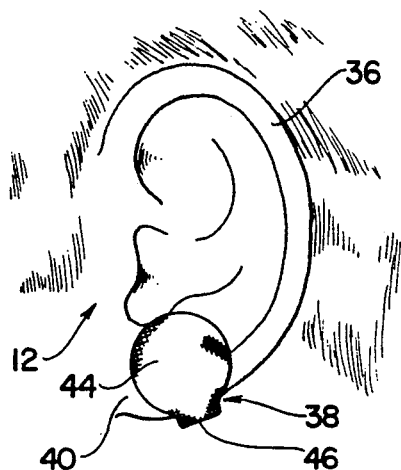
FIG. 6 is an elevational view of a second embodiment of the ear pressure dressing of the instant invention mounted on an earlobe.
Figure 7:
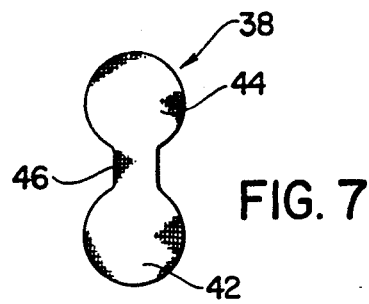
FIG. 7 is an elevational view of the outer surface of the unformed dressing of FIG. 6.

Referring now to the drawings, a first embodiment of the ear pressure dressing of the instant invention is illustrated and is generally indicated at 10 in FIGS. 1 through 5. This particular embodiment of the ear pressure dressing 10 is useful in the treatment of an auricular hematoma which occurs when skin on the anterior side of an ear generally indicated at 12 becomes detached from the underlying cartilage. The ear pressure dressing 10 generally comprises a thin strip of ductile metal generally indicated at 14 and a pair of soft pressure pads 16 which are affixed to opposing ends thereof. The metal strip 14 preferably comprises a ductile aluminum which can be bent into a desired form yet will retain its general shape once formed. The metal strip 14 includes first and second space end portions, 18 and 20, respectively, and a central connector portion 22 which joins the two end portions. The metal strip 14 also includes a first pair of spaced arm portions 24 which project outwardly from the first end portion 18 and extend toward the second end portion 20, and a second pair of spaced arm portions 26 which project outwardly from the second end portion 20 and extend toward the first end portion 18. The metal strip 14 has an inner surface generally indicated at 28 (FIGS. 3 and 4) and an outer surface generally indicated at 30 (FIG. 2) The pressure pads 16 comprise foam sponge pads approximately 5 mm in thickness which are affixed to the inner surfaces 28 of the end portions 18 and 20 by any suitable means, such as an adhesive material 32. It is pointed out that the foam pads 16 may be trimmed to the shape of the injured area before being applied to the metal strip 14. The ear pressure dressing 10 further includes a lining material 34 which is affixed to the inner and outer surfaces 28 and 30 of the metal strip. The lining material 34 may comprise a thin gauze sheet, silicone gel sheeting, or silastic sheeting depending on the type of injury and the intended length of treatment. It has been found that silicone gel sheeting and silastic sheeting are somewhat effective in reducing the formation of scar tissue and therefore these materials may be desirable where the formation of scar tissue on the ear is likely. The lining material 34 may be affixed to the inner and outer surfaces 28 and 30 of the metal strip in any desirable fashion such as with an adhesive material. The preferred method of forming the ear pressure dressing 10 is to have an adhesive material 32 applied to the inner and outer surfaces 28 and 30 of the metal strip 14 and then to have the lining material 34 applied over the entire inner and outer surfaces of the metal strip 14. Selected portions of the lining material 34 may later be removed from the end portions 18 and 20 of the inner surface of the metal strip to expose the adhesive 32 at those areas where it is desired to affix the foam pads 16 thereon, (See FIG. 3). Alternatively, the foam pads 16 may include an adhesive material on one side thereof and may be affixed to the inner surfaces of end portions 18 and 20 without removal of the lining material 34.

In use, the ear pressure dressing 10 is applied over the injured portion of the ear 12 to compress the skin and cartilage together thus preventing the reformation of the hematoma and also encouraging the skin to reattach to the cartilage. To apply the ear pressure dressing 10 to the injured area, the central connector portion 22 is reversely bent so that the pressure pads 16 are positioned in closely spaced, substantially opposed adjacent relation. The first end 18 of the dressing is positioned on the anterior side of the ear 12 and second end 20 on the posterior side of the ear 12 so that the pressure pads 16 are positioned over the injured area. Once the dressing 10 is correctly positioned, the pressure pads 16 are compressed together against the injured area and the spaced arm portions 24 and 26 are bent over and around the peripheral cartilaginous rim portions 36 of the ear to secure the dressing in place. The ductility of the metal strip 14 maintains the pads 16 in pressured engagement with the ear 12, and allows the dressing 10 and arm portions 24 and 26 to be formed to the particular shape of the patient's ear 12. The ductility also allows the dressing 10 to be formed and then reformed thereby permitting the dressing to be easily removed for cleaning and examination of the ear, after which the dressing may be easily reapplied. It is pointed out that the lining material 34 on the inner surface of the dressing may also include an adhesive material on the surface thereof which would help to secure the dressing 10 to the ear 12.

Figure 8:
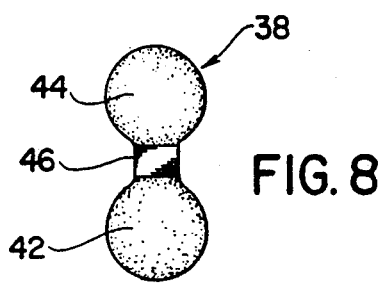
FIG. 8 is an elevational view of the inner surface thereof.
Figure 10:
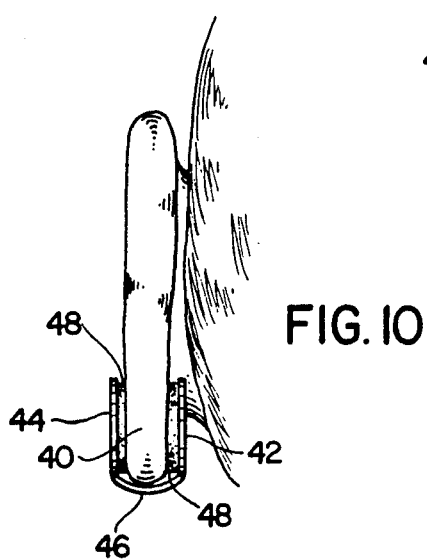
FIG. 10 is a rear view of the second embodiment mounted on the earlobe.
Figure 9:
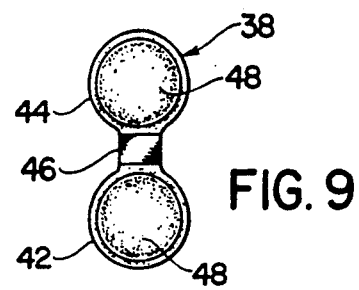
FIG. 9 is a view similar to FIG. 8 with the pressure pads affixed to the end portions thereof.

An alternative embodiment of the ear pressure dressing is illustrated in FIGS. 6 through 10 and it is generally indicated at 38. This embodiment of the ear pressure dressing is useful in the treatment of injuries to the earlobe 40. The earlobe pressure dressing 38 is formed in the same manner as the previously described ear pressure dressing 10 except that the shape has been altered to better suit the shape and size of the earlobe 40. The earlobe pressure dressing 38 comprises first and second generally circular, spaced end portions, 42 and 44, respectively, and a central connector portion 46 which joins the two end portions, thus providing a substantially dumbell-shape configuration. A lining material is affixed to the entire outer surface of the dressing (FIG. 7) and to the inner surface of the central connector portion (FIGS. 8 and 9). Circular foam pads 48 (FIGS. 9 and 10) are affixed to the end portions 42 and 44.

In use, the central connector portion 46 is reversely bent so that the pads 48 are positioned in closely spaced, adjacent relation on opposing sides of the earlobe 40. Once the pads 48 are correctly positioned, they are compressed together so that they engage with the earlobe 40. The dressing 38 is effectively maintained in position by the pressured engagement of the pads 48 against the earlobe 40.

Figure 11:
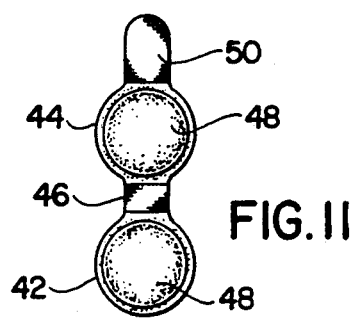
FIG. 11 is an elevational view of the inner side of an alternative form of the second embodiment.
Figure 12:
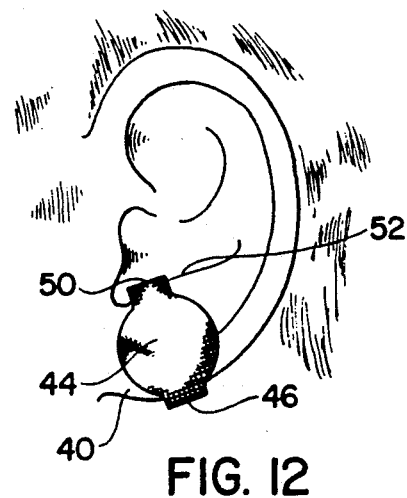
FIG. 12 is an elevational view thereof with the dressing positioned on the earlobe.

An alternative form of the second embodiment is illustrated in FIGS. 11 and 12 wherein the earlobe pressure dressing 38 further includes a tongue portion 50 which extends outwardly from the second end portion 44 thereof. In use, the second end portion 44 is positioned on the anterior side of the earlobe 40 and the tongue portion 50 is bent over and around the lower cartilaginous rim portion 52 of the ear 12 adjacent the earlobe 40. The tongue portion 50 is effective for maintaining the pressure dressing 38 in position during periods of increased physical activity. It is pointed out that all three embodiments of the pressure dressing can be worn during physical activity, and in this regard can even be worn by wrestlers and boxers under their head gear during practice and competition. Should the pressure dressing become dislodged during practice or competition, it will not cause further injury to the ear and it can easily be replaced.

It is seen therefore that the instant invention provides an effective pressure dressing which is adaptable for treating a wide variety of ear injuries. The pressure dressing provides a safe and comfortable method of exerting pressure on an injured portion of the ear which does not require the use of sutures. The dressing is formable to the shape of the patient's ear and it can be easily removed for cleaning and examination of the ear and then replaced. For these reasons it is believed that the pressure dressing of the instant invention represents significant advancements in the art.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. An ear pressure dressing comprising:
  a thin strip of ductile metal having first and second spaced end portions which are joined by a central connector portion, said first and second end portions and said connector portion each having respective inner and outer surfaces;
  a pair of soft pressure pads; and
  means affixing said pads to the inner surfaces of said first and second end portions,
  said connector portion being reversely bendable so that said pads are positionable in closely spaced, substantially adjacent relation, said pads being engageable with opposing sides of an ear, said thin strip of ductile metal being operable for maintaining said pads in pressured engagement with said opposing sides of said ear.

2. The ear pressure dressing of claim 1, wherein said first and second end portions have a substantially round configuration.

3. The ear pressure dressing of claim 1 further comprising a lining material and means for affixing said lining material to the respective inner and outer surfaces of said first and second end portions, and said connector portion.

4. The ear pressure dressing of claim 3, wherein said lining material comprises silicone gel sheeting.

5. The ear pressure dressing of claim 3, wherein said lining material comprises gauze.

6. The ear pressure dressing of claim 3, wherein said lining material comprises silastic sheeting.

7. The ear pressure dressing of claim 1, wherein said pads comprise foam sponge pads.

8. An ear pressure dressing comprising:
  a thin strip of ductile metal having first and second spaced end portions which are joined by a central connector portion, said first and second end portions and said connector portion each having respective inner and outer surfaces;
  a pair of soft pressure pads; and
  means affixing said pads to the inner surfaces of said first and second end portions,
  said connector portion being reversely bendable so that said pads are positionable in closely spaced, substantially adjacent relation, said pads being engageable with opposing sides of an ear, said thin strip of ductile metal being operable for maintaining said pads in pressured engagement with said opposing sides of said ear,
  said thin strip of ductile metal further including a tongue portion extending outwardly from said second end portion, said tongue portion being bendable over and around a cartilaginous rim portion of the ear.

9. An ear pressure dressing comprising:
  a thin strip of ductile metal having first and second spaced end portions which are joined by a central connector portion, said first and second end portions and said connector portion each having respective inner and outer surfaces;
  a pair of soft pressure pads; and
  means affixing said pads to the inner surfaces of said first and second end portions,
  said connector portion being reversely bendable so that said pads are positionable in closely spaced, substantially adjacent relation, said pads being engageable with opposing sides of an ear, said thin strip of ductile metal being operable for maintaining said pads in pressured engagement with said opposing sides of said ear,
  said thin strip of ductile metal further including a first pair of spaced arm portions which project outwardly from said first end portion and extend toward said second end portion, and a second pair of spaced arm portions which project outwardly from said second end portion and extend toward said first end portion,
  said first and second pairs of spaced arm portions being bendable over and around a peripheral cartilaginous rim portion of said ear.

* * * * *